United States Patent
Bergins et al.

(10) Patent No.: US 9,885,257 B2
(45) Date of Patent: Feb. 6, 2018

(54) FLEXIBLY OPERABLE POWER PLANT AND METHOD FOR THE OPERATION THEREOF

(71) Applicant: Mitsubishi Hitachi Power Systems Europe GmbH, Duisburg (DE)

(72) Inventors: Christian Bergins, Datteln (DE); Torsten Buddenberg, Moers (DE); Efthymia-Ioanna Koytsoumpa, Duisburg (DE)

(73) Assignee: MITSUBISHI HITACHI POWER SYSTEMS EUROPE GMBH, Duisburg (DE)

( * ) Notice: Subject to any disclaimer, the term of this patent is extended or adjusted under 35 U.S.C. 154(b) by 110 days.

(21) Appl. No.: 14/904,057

(22) PCT Filed: Jul. 8, 2014

(86) PCT No.: PCT/EP2014/064627
§ 371 (c)(1),
(2) Date: Jan. 8, 2016

(87) PCT Pub. No.: WO2015/010895
PCT Pub. Date: Jan. 29, 2015

(65) Prior Publication Data
US 2016/0237858 A1    Aug. 18, 2016

(30) Foreign Application Priority Data

Jul. 9, 2013 (DE) .................. 10 2013 1 07259
Mar. 12, 2014 (DE) .................. 10 2014 1 03311
Apr. 9, 2014 (DE) .................. 10 2014 1 05067

(51) Int. Cl.
*F01K 23/18* (2006.01)
*C25B 1/02* (2006.01)
(Continued)

(52) U.S. Cl.
CPC .............. *F01K 23/18* (2013.01); *C07C 1/12* (2013.01); *C07C 29/00* (2013.01); *C07C 29/152* (2013.01);
(Continued)

(58) Field of Classification Search
CPC ........ F01K 23/18; F01K 25/103; F01K 3/188; F01K 13/00; F01K 17/02; C07C 29/152;
(Continued)

(56) References Cited

U.S. PATENT DOCUMENTS 4,235,044 A   11/1980   Cheung
5,344,627 A    9/1994   Fujii et al.
(Continued)

FOREIGN PATENT DOCUMENTS

CN   1141027 A    1/1997
CN   1318210 A   10/2001
(Continued)

OTHER PUBLICATIONS

Chinese Office Action and Search Report dated Dec. 28, 2016 for corresponding foreign Application No. 20148004978.4.
(Continued)

*Primary Examiner* — Hoang Nguyen
(74) *Attorney, Agent, or Firm* — Knobbe Martens Olson & Bear LLP (57) ABSTRACT

One embodiment relates to a power plant having a large steam generator, which is equipped with hydrocarbon-fired burners and/or with a gas turbine and which has a water/steam circuit connected thereto, and comprising at least one device for generating a $CO_2$-rich gas flow, wherein the electrical power output of the electricity-generating part, of the power plant to the electrical grid is subject to power regulation controlled, at the power grid side. Some embodiments relate to a flexible operating method for the power (Continued)

plant that is fired with hydrocarbon-containing fuel, which operating method permits in particular a rapid adaptation of the power plant output to the power demands from the grid.

23 Claims, 2 Drawing Sheets (51) Int. Cl.
| | |
|---|---|
| C07C 29/152 | (2006.01) |
| C10L 3/00 | (2006.01) |
| C25B 1/04 | (2006.01) |
| F01K 13/00 | (2006.01) |
| F01K 17/02 | (2006.01) |
| C25B 15/02 | (2006.01) |
| C25B 15/08 | (2006.01) |
| C07C 29/00 | (2006.01) |
| C07C 1/12 | (2006.01) |
| F01K 3/18 | (2006.01) |
| F01K 25/10 | (2006.01) |

(52) U.S. Cl.
CPC ........ C10L 3/00 (2013.01); C25B 1/02 (2013.01); C25B 1/04 (2013.01); C25B 15/02 (2013.01); C25B 15/08 (2013.01); F01K 3/188 (2013.01); F01K 13/00 (2013.01); F01K 17/02 (2013.01); F01K 25/103 (2013.01); Y02E 20/14 (2013.01); Y02E 20/16 (2013.01); Y02E 20/18 (2013.01); Y02E 20/326 (2013.01); Y02E 60/366 (2013.01); Y02P 20/129 (2015.11)

(58) Field of Classification Search
CPC ........... C07C 1/12; C07C 29/00; C25B 31/02; C25B 15/02; C25B 15/08; C25B 1/04; C10L 3/00; Y02E 20/326; Y02E 20/16; Y02E 20/18; Y02E 60/366; Y02E 20/14
USPC .................................................. 60/646, 657
See application file for complete search history.

(56) References Cited

U.S. PATENT DOCUMENTS

| | | | | |
|---|---|---|---|---|
| 5,416,245 | A * | 5/1995 | MacGregor | C01B 3/042 518/703 |
| 7,244,771 | B1 * | 7/2007 | Seymour | C10J 3/00 205/629 |
| 2002/0095938 | A1 | 7/2002 | Wintrell | |
| 2007/0130957 | A1 | 6/2007 | Hoffmann et al. | |
| 2007/0256361 | A1 * | 11/2007 | Kindig | C01B 3/105 48/197 R |
| 2009/0247653 | A1 | 10/2009 | Ravikumar et al. | |
| 2010/0050637 | A1 | 3/2010 | Yamashita et al. | |
| 2010/0156104 | A1 * | 6/2010 | Bottinelli | C01B 3/12 290/52 |
| 2010/0175320 | A1 * | 7/2010 | Schuetzle | C10K 3/026 48/76 |
| 2011/0041740 | A1 | 2/2011 | Reilly | |
| 2011/0229382 | A1 | 9/2011 | Frydman et al. | |
| 2012/0091730 | A1 | 4/2012 | Stuermer et al. | |
| 2012/0238645 | A1 * | 9/2012 | Rudlinger | C10G 2/30 518/700 |
| 2016/0153316 | A1 | 6/2016 | Bergins et al. | |

FOREIGN PATENT DOCUMENTS

| | | |
|---|---|---|
| CN | 101760248 A | 6/2010 |
| CN | 102787993 A | 11/2012 |
| DE | 102006034712 A1 | 1/2008 |
| DE | 102009018126 A1 | 10/2010 |
| DE | 102011013922 A1 | 9/2012 |
| EP | 2532729 A2 | 12/2012 |
| EP | 2543743 A1 | 1/2013 |
| FR | 2939450 A1 | 6/2010 |
| FR | 2977089 A1 | 12/2012 |
| JP | 2013-092065 | 5/2013 |
| WO | WO 2000/016425 | 3/2000 |
| WO | WO 2010/069622 | 6/2010 |
| WO | WO 2011/108546 A1 | 9/2011 |
| WO | WO 2013/029701 | 3/2013 |
| WO | WO 2015/004143 | 1/2015 |

OTHER PUBLICATIONS

Ichikawa et al., "New Technologies for Separation, Fixation and Conversion of Carbon Dioxide to Mitigate Global Warming", Hitachi Review. (1993) 42(6):255-260.
International Search Report and Written Opinion dated Oct. 27, 2014, for International Application No. PCT/EP2014/064625 filed Jul. 8, 2014.
International Search Report and Written Opinion dated Oct. 27, 2014, for International Application No. PCT/EP2014/064627 filed Jul. 8, 2014.
Chinese Office Action dated Mar. 3, 2017 for foreign Application No. 201480049230.5.
Japanese Office Action dated Jan. 31, 2017 for foreign Application No. 2016-524796.
Japanese Office Action dated Apr. 4, 2017 for corresponding Application No. 2016-524797.

* cited by examiner

FIG.2

ND METHOD FOR THE OPERATION THEREOF

FLEXIBLY OPERABLE POWER PLANT AND METHOD FOR THE OPERATION THEREOF

RELATED APPLICATIONS

This application is the U.S. National Phase of Application No. PCT/EP2014/064627 entitled "FLEXIBLY OPERABLE POWER PLANT AND METHOD FOR THE OPERATION THEREOF" filed Jul. 8, 2014, which designated the United States, and which claims the benefit of German Application No. 10 2013 107 259.3 filed Jul. 9, 2013; German Application No. 10 2014 103 311.6 filed Mar. 12, 2014; and German Application No. 10 2014 105 067.3 filed Apr. 9, 2014.

The invention is directed to a power plant which has a large-scale steam generator which is equipped with carbon-fired burners and/or a gas turbine and has a connected water/steam circuit comprising at least one steam-charged turbogenerator having at least one connected generator, wherein a $CO_2$-containing offgas stream is produced in the large-scale steam generator equipped with the carbon-fired burners, and which comprises at least one unit for production of a $CO_2$-rich gas stream, and which is connected by its power-generating component comprising the at least one generator to a public power grid which provides control power, wherein the release of electrical power by the power-generating component to the power grid is subject to power control on the power grid side, especially to primary control and/or secondary control and/or tertiary control and/or quaternary control. The invention is further directed to a method of flexibly operating such a power plant.

Because of increasing and higher-priority feed-in of renewable energies, power plants are nowadays losing valuable periods for production and feed-in of power into the power grids, since they have to be run down in the event of correspondingly high supply of renewable energies. This affects the economic viability of the power plants since less power can be sold than would be producible from a production point of view. At the same time, the power plants have to be operated in order to provide services to the grid, without consumption of or adequate payment for the minimum power fed in, since, when a surplus of power exists on the grid, power prices on exchanges are lower than the marginal costs of generation. For this reason, as well as the throttling of renewable energies, demand-side management in industrial plants and the throttling of large-scale solar power plants and wind farms are now already being used for grid stabilization.

Because of the rising proportion of renewable energies in power supply, situations often arise in which available thermal power plants have to greatly lower their load, since the renewable energies have feed-in priority. This reduces annual power sales from thermal power plants. Moreover, the partial overproduction of power has caused a drop in the price of electrical power on exchanges, which reduces the income of such conventional power plants to the extent of unviability.

The overproduction is additionally aggravated by the fact that thermal power plants are nevertheless constantly required on the grid, for example for primary control, but are restricted with regard to power production in terms of their power or load regulation by what is called the minimum load, which exists for technical reasons. This minimum load in the case of large-scale brown coal power plants, for example, is 30%-50%, and in the case of hard coal power plants 15% to 30%, of the nominal output. Thus, the power plants provide services for grid stabilization but lose money as a result of the feed-in of power as a result of excessively low exchange prices.

In order to provide a remedy here, there are known "power to heat" applications in which surplus power is used in electrical hot water or steam generators. This can be stored directly in the heating system of residential buildings or in large heat storage means at power plants for later district heat supply. This application has the advantage of very low capital costs. A disadvantage here is that, because of the heat losses, only a short storage time in the region of a few days at most is possible. Moreover, in this method, heat is produced at a low exergy level from power, which is a high-value energy form (pure exergy).

Another possibility for flexibilization and the lowering of the minimum load in the power plant would be to store the thermal energy generated directly in the steam circuit of the power plant. This could be done in the form of steam in what are called Ruths accumulators in the steam circuit of the power plant. However, the storable amounts of energy and the storage periods, which are particularly in the region of less than 60 min, are quite low.

Another alternative possibility is heat storage in the form of hot water in the preheating zone of the steam circuit of power plants. But here too, the storable amounts of energy are small. An alternative is heat storage at relatively high temperature in the form of hot liquid salts (temperature change) or as phase change energy of salts or other solids. Here, however, the systems are untested and are difficult to implement.

There is practical knowledge of the preparation of synthesis gas with subsequent preparation of hydrogen and/or methane and/or chemical conversion products in what are called fuel gasification plants, which can also be coupled to gas turbine power plants given suitable configuration for power generation. However, these "integrated gasification combined cycle" (IGCC) plants are quite complex, costly and inflexible. More particularly, they are slow in the changeover between the modes of operation of power production and chemical production (e.g. methanol) and in the changeover of the fuels used, since, as well as the fuel gasifier, components that are necessarily present such as a gas purification/gas processing operation or a $CO_2$ separation are also sluggish processes and plants. Moreover, plant availability is reduced in the dynamic operation of such plants, if the required availability or the technological peculiarities of the individual process do not indeed make the highly dynamic operation completely impossible. Moreover, in these processes, the chemical conversion products prepared on the basis of the carbon that originates from the fuel are produced by a direct chemical route, which usually leads to higher carbon conversion efficiencies and hence also energy conversion levels. For example, up to more than 50% of the fuel carbon can be converted to the methane product. At the same time, however, the capital costs per kWel of installed power are between 50% and 100% above those of a standard thermal power plant. Moreover, there are only very few IGCC plants worldwide. For these reasons, fuel gasification has to date been employed globally only in the cases where high-value chemical products such as fuels or fertilizers are produced from solid carbonaceous fuels, usually coal, in plants which are effectively run in baseload operation.

It is also known that $CO_2$ is one of the greenhouse gases which are considered to be one of the causes of the heating of the global climate. Therefore, there are numerous efforts in environmental policy and technology to reduce $CO_2$ output. One of these concepts is concerned with the storage of $CO_2$ by the conversion of $CO_2$ to methane gas and is described, for example, in the article "New technologies for separation, fixation and conversion of carbon dioxide to mitigate global warming" (Hitachi, vol. 42 (1993), no. 6, pages 255-260). In this case, the $CO_2$ that forms during the combustion of fossil fuels is separated out of the flue gas and sent to methanization in which synthetic natural gas (methane) forms. Methanization is a chemical reaction in which carbon monoxide (CO) or carbon dioxide ($CO_2$) is converted to methane ($CH_4$). The reaction of carbon dioxide to give methane is also referred to as the Sabatier process and was discovered in 1902 by Paul Sabatier and J. B. Sendersens. In this reaction, carbon monoxide or carbon dioxide reacts at temperatures of 300-700° C. with hydrogen to give methane and water. The reaction is exothermic but has to be accelerated by a catalyst.

Moreover, in connection with the generation of renewable energy by means of wind power or solar energy, the problem arises that more power is frequently being fed into the grid than is currently being demanded. This leads to an amount of "surplus power" which has to be consumed or stored in order to assure grid stability. Even independently of the feed-in of power generated from a renewable energy source into a grid, the basic problem arises of being able to store power generated if necessary, in order to be able to utilize this energy at any given time.

In this connection, the "power to gas" concept has been found to be advantageous, in which the energy is converted chemically by means of methanization and stored as methane ($CH_4$). In this case, the hydrogen needed for the formation of the methane is especially produced by means of an electrolysis which obtains the power required from a renewable energy source such as wind turbines or solar cells. Possible $CO_2$ or CO sources are processed flue gas streams from power plants or industrial plants in which carbonaceous fuel or carbonaceous feedstocks are converted to a $CO_2$- or CO-containing gas atmosphere.

The "power to gas" concept is a viable method of longer-term energy storage and avoidance of direct $CO_2$ emissions into the atmosphere, since the methane product ($CH_4$) formed in the methanization can be stored in the long term as synthetic natural gas in existing infrastructure installations (pipelines, natural gas reservoirs) over periods of months. The hydrogen can be prepared by electrolysis. Alternatively, the hydrogen may also originate from other alternative sources. The $CO_2$ may originate from a separation from a $CO_2$-rich stream, for example the flue gas stream from a power plant. The $H_2$ and $CO_2$ components obtained in this way are converted in a methanization plant or a methanator by synthesis to $H_2O$ and $CH_4$.

It is an object of the invention to provide a solution which provides a flexible way of running or mode of operation of a carbonaceous fuel-fired power plant, and which especially enables timely adjustment of the power plant output to grid-side power demands.

This object is achieved in accordance with the invention by a power plant having the features of claim 1 and a method of operating such a power plant as claimed in claim 16.

Appropriate configurations and advantageous developments of the invention are the subject of the particular dependent claims.

The above object is thus achieved in a power plant of the type specified in detail at the outset in that the power plant comprises at least one electrolysis plant for preparation of hydrogen and at least one synthesis plant for preparation of methanol and/or methanol conversion products from at least $CO_2$ components of the $CO_2$-rich gas stream and the hydrogen produced in the electrolysis plant, and in that the at least one unit for production of a $CO_2$-rich gas stream and the at least one electrolysis plant for preparation of hydrogen ($H_2$) and the at least one synthesis plant for preparation of methanol and/or methanol conversion products from at least $CO_2$ components of the $CO_2$-rich gas stream and the hydrogen produced in the electrolysis plant are connected physically and electrically to one another in terms of conduction by means of current-conducting and by means of media-conducting lines in such a way that the power generated on the power plant side in the course of operation of the power plant is utilizable wholly or partly, as required, for operation of one, more than one or all of this group of units and plants consisting of the at least one unit for production of a $CO_2$-rich gas stream, the at least one electrolysis plant for preparation of hydrogen ($H_2$) and the at least one synthesis plant for preparation of methanol and/or methanol conversion products.

In a method of flexibly operating a power plant as claimed in any of claims 1-15, the above object is achieved in that the at least one unit for production of a $CO_2$-rich gas stream and the at least one electrolysis plant for preparation of hydrogen ($H_2$) and the at least one synthesis plant for preparation of methanol and/or methanol conversion products from at least $CO_2$ components of the $CO_2$-rich gas stream and the hydrogen produced in the electrolysis plant have been and are connected physically and electrically to one another in terms of conduction by current-conducting and media-conducting lines such that the power generated on the power plant side in the course of operation of the power plant is utilized wholly or partly, as required, for operation of one, more than one or all of this group of units and plants consisting of the unit for production of a $CO_2$-rich gas stream, the electrolysis plant for preparation of hydrogen ($H_2$) and the synthesis plant for preparation of methanol and/or methanol conversion products.

In a first aspect, the starting point the invention is to flexibilize a power plant fired with carbonaceous fuel by the integration of a production of a $CO_2$-rich gas stream, especially a $CO_2$ separation, a hydrogen-producing electrolysis and a chemical synthesis for preparation of methanol and/or methanol conversion products, for example dimethyl ether (DME) or gasoline.

Flexibilization is understood here to mean that the power plant (regularly) produces not only the products of power and services to the grid, for example primary control and secondary control, but also further products, for example methanol, DME, gasoline or further raw materials for the chemical or petrochemical industry or the transport industry. In addition to this there is also the product of demand-side management (i.e. the enablement of lowering of the grid load by reduction of the process power demand).

In addition, flexibilization is understood to mean that the combination of such processes can further lower the minimum feed of a power plant or power plant site and can reduce it to negative values without having to shut down the power plant. This is particularly advantageous when the power plant, in spite of sufficient power producers available on the grid, for example renewable power generators, which would otherwise have to be curtailed, is still to remain connected to the grid for grid control and stabilization.

The invention encompasses power plants wherein the carbon-fired burners are operated with carbonaceous biogenic renewable raw materials, hard coal, brown coal, carbonaceous waste materials from industry, carbonaceous gaseous fuels such as natural gas, biogas or mixtures of carbonaceous gases such as co-produced gases from the chemical industry or steel production. The invention is employable in steam power plants where the fuels are combusted in a steam generator or else in gas turbine plants or gas engines in which liquid or gaseous carbonaceous fuels are combusted, or else combinations of these power plants, for example gas turbine and steam turbine power plants, called combined cycle power plants. The invention is also applicable to the offgases from cement furnaces, plants in the paper industry and other combustion processes, provided that the corresponding plant/installation includes downstream steam production and a steam turbine for utilization of at least some of the waste heat for power generation.

If the minimum load of the power plant of the power plant is to be reduced further in accordance with the invention by the internal use of the power generated on the power plant side in a "power to fuel" (PtF) process or surplus power is even to be drawn from the grid, it is possible with the aid of the power to prepare hydrogen ($H_2$) in a water electrolysis (or else alternatively by a chlor-alkali electrolysis) and additionally to separate carbon dioxide ($CO_2$) out of the flue gases, which reduces power generation further. This $CO_2$ and $H_2$ is used in accordance with the invention in a chemical synthesis by a catalytic process to prepare methanol, for example, which can subsequently be processed further.

This gives rise to the possibility of achieving a higher annual utilization time of the power plant in power plant operation and also of achieving viable operation (again) through the extension of the product range (preparation of methanol or methanol conversion products). This becomes possible without requiring "capacity mechanisms" which subsidize an unviable power plant for standby operation, i.e. support the operation of an otherwise unviable power plant installation by special payment to the power plant operator in order to promote grid stability.

The invention thus proceeds from the idea of storing the surplus power produced in the form of methanol or methanol conversion products in the chemical energy of the substances outside the power grid and the steam circuit and subsequently of using them in a suitable manner in the power plant or outside for other purposes.

The flexibilization of the power plant is thus achieved firstly through product flexibilization. This means that the power plant is set up not just in relation to the production of the "power" product but additionally also set up in relation to the production of the "methanol and/or methanol conversion products" products. In this context, the power plant is additionally configured in such a way that flexible variation is possible between the amount of power and methanol or conversion products thereof produced in each case. This can be achieved easily by inserting appropriate current-conducting and media-conducting connections between the individual plants or units and optionally setting up storage means or intermediate storage means for the product produced or reactant to be processed in the particular plant or unit. Secondly, the flexibilization relates to operational flexibilization, i.e. flexibilization of the possible mode of operation of a power plant of the invention. By virtue of a constituent of the power plant or of the overall power plant system being a hydrogen-producing electrolysis, an otherwise non-standard power consumer is present, which can be operated with power generated on the power plant side as an alternative to the feeding of the power generated on the power plant side into the connected public power grid. The electrolysis plants for preparation of hydrogen have the advantage that they react relatively quickly to power consumption and hence can be quickly run up—or run down—in terms of their current/power consumption and their production or conversion output. It is also possible to use surplus power that exists in the connected public power grid in the electrolysis plant(s). The plants and units of the invention have likewise been equipped with further power consumers which can rapidly consume power. Thus, more particularly, a change in the current/power consumption and the production or conversion output of the electrolysis plant(s) for preparation of hydrogen and/or the synthesis plant(s) for preparation of methanol and/or methanol conversion products and/or the unit(s) for production of a $CO_2$-rich gas stream can be achieved at short notice, preferably in the range of minutes.

It is therefore a feature of the invention, in terms of the configuration of the power plant, that the at least one electrolysis plant for preparation of hydrogen ($H_2$) or a plurality of electrolysis plants for preparation of hydrogen ($H_2$) is/are designed and set up on the power plant side in terms of their current/power consumption capacity and their hydrogen production capacity so as to be controllable in such a way that the current/power consumption and hydrogen production thereof can be run up or down at short notice, preferably in the minute range, in response to a grid-side power control demand on the power plant. In an analogous manner, it is a feature of the method of the invention, in terms of configuration, that the current/power consumption and the hydrogen production in the at least one electrolysis plant for preparation of hydrogen ($H_2$) or the plurality of electrolysis plants for preparation of hydrogen ($H_2$) is run up or down at short notice, preferably in the minute range, on the power plant side in response to a grid-side power control demand on the power plant.

It is advantageous here when not just the electrolysis plant but also the unit(s) for production of a $CO_2$-rich gas stream and the synthesis plant for preparation of methanol and/or methanol conversion products promote the flexible way of running or mode of operation of the power plant. Therefore, it is a feature of a development of the power plant that the at least one unit for production of a $CO_2$-rich gas stream or a plurality of units for production of a $CO_2$-rich gas stream and/or the at least one synthesis plant for preparation of methanol and/or methanol conversion products from at least portions of the $CO_2$-rich gas stream or a plurality of synthesis plants for preparation of methanol and/or methanol conversion products from at least portions of the $CO_2$-rich gas stream is/are designed and set up on the power plant side in terms of their current/power consumption capacity and their production or conversion capacity so as to be controllable in such a way that their respective current/power consumption and production or conversion output can be run up or down at short notice, preferably in the minute range, in response to a grid-side power control demand on the power plant.

Running individual or several plants or units of the power plant up or down at short notice, preferably in the minute range, is understood above and hereinafter in the context of this application to mean that running-up or -down is effected within 30 s as a reaction to a grid-side primary control demand and within 5 min as a reaction to a grid-side secondary control demand, unless any different specifications are made in the individual case in the description which follows.

In the same way, in a development of the method of the invention, the respective current/power consumption and production or conversion output of the at least one unit for production of a $CO_2$-rich gas stream or a plurality of units for production of a CO$_2$-rich gas stream and/or the at least one synthesis plant for preparation of methanol and/or methanol conversion products from at least portions of the CO$_2$-rich gas stream or a plurality of synthesis plants for preparation of methanol and/or methanol conversion products from at least portions of the CO$_2$-rich gas stream is run up or down at short notice, preferably in the minute range, on the power plant side in response to a grid-side power control demand on the power plant.

Since, in the power plant of the invention, it is possible to feed the power generated by means of the at least one generator very rapidly and at short notice not just into the connected power grid but also to distribute it among the plants and units present in accordance with the invention, a power plant of the invention can undergo a rapid change in load. It is therefore a further feature of the invention that the at least one electrolysis plant for preparation of hydrogen (H$_2$) or the plurality of electrolysis plants for preparation of hydrogen (H$_2$) and the at least one unit for production of a CO$_2$-rich gas stream or the plurality of units for production of a CO$_2$-rich gas stream and the at least one synthesis plant for preparation of methanol and/or methanol conversion products from at least portions of the CO$_2$-rich gas stream or the plurality of synthesis plants for preparation of methanol and/or methanol conversion products from at least portions of the CO$_2$-rich gas stream are designed and connected to one another for control purposes on the power plant side in terms of their respective current/power consumption capacity and their respective production or conversion output in such a way that they can be run up or down in response to a grid-side power control demand on the power plant in the integrated system, each in terms of their respective current/power consumption and production or conversion output, at such short notice, preferably in the minute range, that the power plant, in the case of a grid-side power control demand, can be adjusted to the altered power demand in terms of output by way of a change in load with a load change gradient in the range of 3%/min-30%/min.

In order to enable a particularly rapid and short-notice adjustment of the current/power consumption of the individual plants/plant components or units, it is appropriate when they are designed for a long-lasting nominal load or a standard design value or standard operating value, but can be operated at short notice with a much higher peak load by comparison. In terms of configuration, it is therefore a further feature of the invention for the power plant that the at least one electrolysis plant for preparation of hydrogen (H$_2$) or the plurality of electrolysis plants for preparation of hydrogen (H$_2$) and the at least one unit for production of a CO$_2$-rich gas stream or the plurality of units for production of a CO$_2$-rich gas stream and the at least one synthesis plant for preparation of methanol and/or methanol conversion products from at least portions of the CO$_2$-rich gas stream or the plurality of synthesis plants for preparation of methanol and/or methanol conversion products from at least portions of the CO$_2$-rich gas stream is/are designed in terms of their respective current/power consumption and/or their respective production or conversion output in such a way that it/they can be subjected, especially in response to a grid-side power control demand on the power plant, for short periods within the minute range, preferably over a period of up to 30 minutes, to a current/power consumption of 100%-300%, preferably 150%-200%, of the standard design or standard operating value for the particular plant or unit.

In order to achieve particularly good flexibilization of the power plant, it is helpful when the individual plants or units can be adjusted singly and individually to different modes of operation of the power plant, or allow them, both in relation to their power consumption or current/power consumption and in relation to their product output or conversion output. It is therefore also a feature of the invention, in a further configuration of the power plant, that the at least one electrolysis plant for preparation of hydrogen (H$_2$) or the plurality of electrolysis plants for preparation of hydrogen (H$_2$) and the at least one unit for production of a CO$_2$-rich gas stream or the plurality of units for production of a CO$_2$-rich gas stream and the at least one synthesis plant for preparation of methanol and/or methanol conversion products from at least portions of the CO$_2$-rich gas stream or the plurality of synthesis plants for preparation of methanol and/or methanol conversion products from at least portions of the CO$_2$-rich gas stream can be actuated and controlled individually in terms of their respective current/power consumption and their respective production or conversion output. In an analogous manner, in a configuration of the method of the invention, the at least one electrolysis plant for preparation of hydrogen (H$_2$) or the plurality of electrolysis plants for preparation of hydrogen (H$_2$) and the at least one unit for production of a CO$_2$-rich gas stream or the plurality of units for production of a CO$_2$-rich gas stream and the at least one synthesis plant for preparation of methanol and/or methanol conversion products from at least portions of the CO$_2$-rich gas stream or the plurality of synthesis plants for preparation of methanol and/or methanol conversion products from at least portions of the CO$_2$-rich gas stream are actuated and controlled individually in terms of their respective current/power consumption and their respective production or conversion output.

In order to be able to flexibly operate a power plant in which a CO$_2$-containing offgas is produced in the context of the present invention, it is advantageous and appropriate when the at least one synthesis plant for preparation of methanol and/or methanol conversion products or the plurality of synthesis plants for preparation of methanol and/or methanol conversion products is/are designed overall in terms of capacity such that it/they can be used to convert 10%-50% by weight, especially 30%-40% by weight, preferably 35% by weight, of the CO$_2$ which forms at full load of the power plant and is present in the CO$_2$-containing offgas stream to methanol and/or a methanol conversion product, which is likewise envisaged by the invention.

It is additionally also appropriate and advantageous that the at least one synthesis plant for preparation of methanol and/or methanol conversion products or the plurality of synthesis plants for preparation of methanol and/or methanol conversion products is/are designed overall with regard to their current/power consumption capacity and the production or conversion output possible in each case, in terms of capacity, such that not more than the total amount of electrical power that can be generated by the power plant at full load and/or maximum power thereof can be utilized for the preparation of methanol and/or methanol conversion products, which is likewise a feature of the power plant in terms of configuration.

The unit for production of a CO$_2$ gas stream may especially comprise CO$_2$ separation plants which scrub or filter the CO$_2$ (carbon dioxide) out of the offgas formed in the combustion of carbonaceous fuel or obtain it therefrom. It is therefore also a feature of the power plant, in a further configuration, that the at least one unit for production of a CO$_2$-rich gas stream or the plurality of units for production of a CO$_2$-rich gas stream comprise(s) or consist(s) of at least one CO$_2$ separation plant, especially a post-combustion capture (PCC) plant, and/or one or more burner(s) or burner device(s), operated by the oxyfuel process, of the large-scale steam generator having a dedicated $CO_2$ separation plant. In the case of oxyfuel operation of the burners, the oxygen required for the purpose may advantageously also originate especially from an electrolysis plant (or one of the electrolysis plants) for preparation/production of hydrogen in which water is converted to hydrogen ($H_2$) with production of oxygen ($O_2$).

It is additionally advantageous when the plants that enable and affect product flexibilization, in terms of their current/power consumption and their production or conversion output, are designed overall in such a way that the power plant can be operated with its minimum load necessary for the purposes of the plant without feeding power into the power grid, and so all the power that then arises flows into the corresponding plants and/or units that serve for product flexibilization. The invention therefore further envisages a power plant in which the at least one electrolysis plant for preparation of hydrogen ($H_2$) or the plurality of electrolysis plants for preparation of hydrogen ($H_2$) and the at least one unit for production of a $CO_2$-rich gas stream or the plurality of units for production of a $CO_2$-rich gas stream and the at least one synthesis plant for preparation of methanol and/or methanol conversion products from at least portions of the $CO_2$-rich gas stream or the plurality of synthesis plants for preparation of methanol and/or methanol conversion products from at least portions of the $CO_2$-rich gas stream are designed with regard to their current/power consumption and production or conversion output overall in such a way that, in the course of operation thereof, the power plant can be operated in operation with its minimum load necessary for the purposes of the plant without feeding power into the power grid.

In an alternative version, the power plant is to be operable with surplus power from the connected power grid. It is therefore also a feature of the power plant of the invention, in terms of configuration, that the power plant takes the form of a power sink for the connected public power grid, in which case the at least one electrolysis plant for preparation of hydrogen ($H_2$) or the plurality of electrolysis plants for preparation of hydrogen ($H_2$) and the at least one unit for production of a $CO_2$-rich gas stream or the plurality of units for production of a $CO_2$-rich gas stream and the at least one synthesis plant for preparation of methanol and/or methanol conversion products from at least portions of the $CO_2$-rich gas stream or the plurality of synthesis plants for preparation of methanol and/or methanol conversion products from at least portions of the $CO_2$-rich gas stream are designed in terms of their current/power consumption and production or conversion output overall and are connected to the power grid in such a way that they can be operated with the surplus power drawn from the power grid.

In order to be able to make a contribution to the power control of the public power grid, in a further configuration of the invention, the at least one electrolysis plant for preparation of hydrogen ($H_2$) or the plurality of electrolysis plants for preparation of hydrogen ($H_2$) and the at least one unit for production of a $CO_2$-rich gas stream or the plurality of units for production of a $CO_2$-rich gas stream and the at least one synthesis plant for preparation of methanol and/or methanol conversion products from at least portions of the $CO_2$-rich gas stream or the plurality of synthesis plants for preparation of methanol and/or methanol conversion products from at least portions of the $CO_2$-rich gas stream are connected physically and public to the public power grid as a load that can be switched off.

In a configuration of the method of the invention, in an analogous manner, the at least one electrolysis plant for preparation of hydrogen ($H_2$) or the plurality of electrolysis plants for preparation of hydrogen ($H_2$) and the at least one unit for production of a $CO_2$-rich gas stream or the plurality of units for production of a $CO_2$-rich gas stream and the at least one synthesis plant for preparation of methanol and/or methanol conversion products from at least portions of the $CO_2$-rich gas stream or the plurality of synthesis plants for preparation of methanol and/or methanol conversion products from at least portions of the $CO_2$-rich gas stream are operated as a load connected physically and electrically to the public power grid that can be switched off.

In the case of the proposed flexibilization of the power plant in accordance with the invention, it may additionally be advantageous and appropriate to combine heat that arises within the power plant as well in a heat-importing and/or heat-exporting manner. One inventive option, in a development of the invention, is that the at least one electrolysis plant for preparation of hydrogen ($H_2$) or the plurality of electrolysis plants for preparation of hydrogen ($H_2$) and the at least one unit for production of a $CO_2$-rich gas stream or the plurality of units for production of a $CO_2$-rich gas stream and the at least one synthesis plant for preparation of methanol and/or methanol conversion products from at least portions of the $CO_2$-rich gas stream or the plurality of synthesis plants for preparation of methanol and/or methanol conversion products are conductively connected in terms of waste heat that arises in the operation of these plant(s) and/or unit(s) in the range of 30-400° C., preferably in the range of 30-150° C., via at least one waste heat-conducting conduit to a preheater of the feed water of the water/steam circuit and/or a preheater of a $CO_2$ separation plant, especially a post-combustion capture (PCC) plant, and/or a preheater of at least one of the reactants used and/or products generated in the power plant.

In terms of plant technology, it is additionally advantageous when the hydrogen producible with the electrolysis plant is sufficient to convert all the carbon dioxide ($CO_2$) produced or separated out in power plant operation to methanol and/or one or more methanol conversion products. The invention therefore envisages, in a further configuration of the power plant, that the at least one electrolysis plant for preparation of hydrogen ($H_2$) or the plurality of electrolysis plants for preparation of hydrogen ($H_2$) is/are designed in terms of their production and/or conversion capacity in such a way that the amount of hydrogen that can be produced can be used to convert the entire $CO_2$ content of the offgas stream that forms in the burners of the large-scale steam generator in the course of combustion of carbonaceous fuel and/or the total amount of $CO_2$ separated out in the at least one $CO_2$ separation plant to methanol or a methanol conversion product in the synthesis plant(s) for preparation of methanol and/or methanol conversion products.

Finally, it is also a feature of the invention that each of the units or plants from the group of the at least one unit for production of a $CO_2$-rich gas stream, the at least one electrolysis plant for preparation of hydrogen ($H_2$) and the at least one synthesis plant for preparation of methanol and/or methanol conversion products has at least one dedicated reactant and/or product storage means, and the electrolysis plant especially has a dedicated hydrogen storage means and/or an oxygen storage means and the unit for production of a $CO_2$-rich gas stream especially has a dedicated $CO_2$ storage means. These storage means preferably take the form of buffer storage means, such that the processes that proceed in the individual plants/units can be run independently of one another and there is no disruption of the dynamics of the individual processes. In this respect, the storage means also contribute to flexibilization of the operation or the way of running the power plant. Priority in the weighting of the individual plants/units and the processes or methods that proceed therein in each case is possessed by the preparation of methanol and/or methanol conversion products. The capacities and outputs, especially of the $CO_2$ separation plant(s) and the electrolysis plant(s), are adjusted with respect thereto in each case.

With regard to the flexibility of plant operation, the invention of power generation in a power plant fired with carbonaceous fuels with downstream $CO_2$ separation (post-combustion capture, PCC) or integrated $CO_2$ separation (oxyfuel), described here and hereinafter, offers the advantage that the power plant process can be run highly flexibly with regard to the power generation volume. The method can be combined with newly constructed thermal power plants or else as an extension that can be retrofitted onto existing power plant installations. Although the conversion pathway via power generation and electrolysis is nonoptimal in terms of exergy, the energy and exergy drawbacks of this combination of methods can at least partly be compensated for again by particularly advantageous energy connections of the processes. By means of the production of carbonaceous energy carriers (methanol or methanol conversion products), it is even possible in the case of power plants fired with carbonaceous fuels to adjust the minimum load thereof to negative values (0 to >−10.0%). It is likewise possible to increase the primary control capacity to more than 100 $MW_{el}$ per minute, even in the case of relatively small power plant units.

Thus, various advantages arise from the thermal connection of downstream method components, such as that of the $CO_2$ separation downstream of the post-combustion capture principle, and of the hydrogen electrolysis and the downstream methanol or methanol conversion product preparation.

For instance, the waste heat from plant components such as the $CO_2$ separation or the reactors (methanol preparation or conversion) can be incorporated in an energetically favorable manner into the high-pressure preheater or low-pressure preheater of the power plant, or else used for preheating of reactants upstream of the reactors.

Heat needed to operate plant components such as the desorption in the PCC process or any optional downstream rectification or distillation of the products can be taken from the waste heat of reaction from the reactors (methanol preparation or conversion) or be taken in an energetically efficient manner as bleed steam from the steam-raising process or else be obtained at least partly from the cooling of products and intermediates. As a result, the conversion efficiency of power to the respective chemical products is increased significantly to more than 70%, compared to less than 60% in the case of plants having no such energy integration.

If the $CO_2$ separation takes place by the PCC method, the chemical absorption should sensibly, if necessary, have an upstream flue gas desulfurization and/or flue gas cooling operation, in order also to conduct the $CO_2$ separation in a highly efficient manner and with minimum scrubbing agent consumption (usually amine solutions).

Water obtained from the cooling of products or intermediates should, after any purification necessary, preferably be sent back to the hydrogen electrolysis. The purification can preferably be effected in the plants for feed water processing for the power plant and/or else in a water processing system specially designed for the purpose.

In order that the full speed of the change in electrolysis load can be used to support the control capacity of the power plant or within the context of demand-side management, it is appropriate to integrate storage means for water and/or hydrogen and/or $CO_2$ and/or oxygen into the overall process, which permit a delay in the change of load of the chemical reactors or the $CO_2$ separation in the range from seconds up to hours. These may be, for example, pressurized storage means (pressure vessels or caverns) or else liquid storage means. It is thus possible to change the load on the electrolysis by up to 100% within the range of a few seconds via the electrical power applied, while the $CO_2$ separation and downstream reactors can take a longer time for the change in load.

The components of the overall plant (plant complexes of power plant+hydrogen electrolysis+$CO_2$ separation+reactors) can either be run anti-proportionally with respect to the power demand on the grid, i.e. high load on the electrolysis, $CO_2$ separation and/or the reactors (methanol preparation and conversion to methanol conversion products), especially when there is low power demand on the grid while the power plant itself is operated at the lowest possible load, or else controlled in a decoupled manner in such a way that the hydrogen electrolysis, the $CO_2$ separation and the reactors are generally run at maximum load and are only throttled in the case of a positive load demand from the power grid, i.e. are run down in terms of their current/power consumption (demand-side management, DSM).

This latter way of operating the plant or power plant is viable especially when the price level on power exchanges is very low and/or positive load gradients (feed-in) frequently have to be run, since a high additional power feed-in can be achieved very quickly by an instantaneous and immediate shutdown of the hydrogen electrolysis.

In the former case, according to the current plant output, it is possible to support load gradients in the power plant output in either direction (positive or negative) by a very rapid rise in load or drop in load of the hydrogen electrolysis.

The overall dynamics of the system can additionally be supported by the parallel connection of battery systems which can appropriately be integrated at a low voltage level in parallel to hydrogen electrolyses. The size and design of such a battery can be effected with reference to the expected power price level and the capacity utilization of the power plant, and also the expected control interventions for stabilization of the power grid.

The aforementioned methods of storing heat in the steam circuit or from electrical heat generation can also be combined advantageously with the method of the invention.

If the power plant is close to an industrial plant in which oxygen is required, for example in the steel industry or chemical industry, it is appropriate to use the oxygen formed in the performance of an electrolysis of water in these industrial plants and simultaneously to reduce the output of any air fractionation plants present therein.

Otherwise, the oxygen can also be used fully or partly to promote the firing of the power plant to increase the boiler efficiency by the reduction of the offgas volume flow rate or in a pure oxyfuel firing with integrated $CO_2$ separation as an alternative to the PCC $CO_2$ separation.

If neither use in a nearby industrial operation nor use in oxygen-enriched firing is possible or desirable, the oxygen, after any purification and drying necessary, can also be compressed to a higher level and sold on the market as compressed oxygen or, after liquefaction, as liquid oxygen.

The implementation of such downstream processes further increases the power consumption of the overall process and can sensibly be utilized to extend the load control range down to negative power feed-ins (=power consumption) of the power plant or industrial site.

In the method described here for flexibilization of a power plant, according to the configuration and fuel used, with exploitation of the full internal power generation, irrespective of the load range, in the steady state, it is possible to convert about 10%-35% of the carbon present in the fuel or flue gas to methanol and methanol conversion products. The use of power additionally drawn from the grid allows this proportion to be increased further up to more than 90%. Moreover, in the case of use of storage means for the $CO_2$, $H_2$, $O_2$ intermediates, it is temporarily possible to decouple the operation from power generation in the power plant. In addition, it is also possible, via the design of the hydrogen electrolysis for lower current densities in normal operation, to increase the output of the electrolysis significantly up to values of more than 200% of normal operation temporarily and at short notice, in order to consume more power and to support the changes in load in the power feed-in with this negative gradient.

The invention is elucidated in detail by way of example hereinafter with reference to a drawing. This shows, in FIG. 1: in schematic form, a plant flow diagram of a power plant of the invention and, in FIG. 2: likewise in schematic form, the interconnection of a power plant of the invention with dedicated components.

Figure 1:
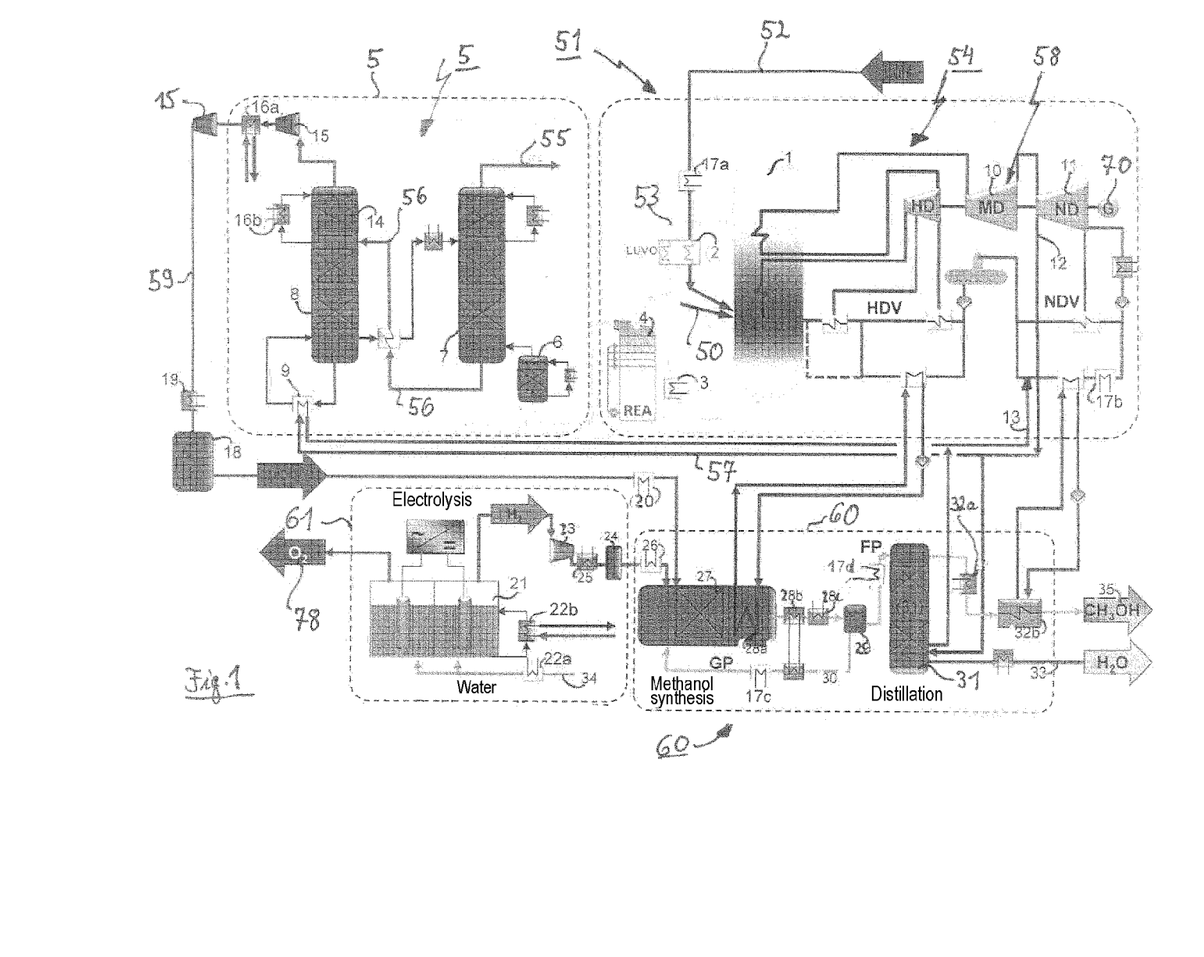

FIG. 1 shows, in schematic form, a power plant 51 fired with brown coal 50, which comprises a large-scale steam generator 1 with a connected water/steam circuit 54. The flue gas 53 formed in the firing of the brown coal 50 in the burners of the large-scale steam generator 1 is fed in a conduit to an air preheater 2 to which is fed, in countercurrent, the combustion air 52 which is supplied through a conduit and is preheated in the air preheater 2. Thereafter, the flue gas 53 is fed to a heat displacement system 3 and heat which is extracted from the flue gas 53 is provided to the feed water preheater of the water/steam circuit 54. Thereafter, the flue gas 53, in terms of conduction, is passed into a flue gas desulfurization plant 4 where it is substantially freed of $SO_2$ (sulfur dioxide) and $SO_3$ (sulfur trioxide). The flue gas 53 cleaned in this way leaves the flue gas desulfurization plant 4 with a temperature of 40-90° C. In order to achieve and to assure high availability and high separation rates in the post-combustion capture (PCC) $CO_2$ separation plant 5 connected downstream of the steam generator 1, the flue gas 53 is first subjected to a fine purification in a fine purification plant 6. The fine purification plant 6 takes the form of a flue gas cooler with a dedicated NaOH (sodium hydroxide) pre-scrubber in which scrubbing of the flue gas 53 with an NaOH solution takes place and the flue gas 53 is cooled to a temperature of 30-50° C. At the same time, the $SO_2/SO_3$ concentration of the flue gas 53 is lowered further.

From the fine purification plant 6, the cooled flue gas 53 is introduced into an absorber 7 of the post-combustion capture (PCC) plant 5 and contacted therein, in countercurrent, with a scrubbing agent which leaches the $CO_2$ out of the gas stream. The $CO_2$ scrubbing agent in the working example is an aqueous amine solution which takes the form of a simple monoethanolamine solution, such that the energy demand in the downstream desorption in the desorber 8 is 3.2-3.8 MJ/kg of carbon dioxide removed. Alternatively, it is also possible to use a $CO_2$ scrubbing agent which is optimized in relation to the energy demand necessary in the desorption such that only an energy demand in the range of 2.4-2.8 MJ/kg of carbon dioxide removed is now required therein. Departing from the absorber are firstly a cleaned gas 55 and secondly the $CO_2$-saturated $CO_2$ scrubbing agent solution, which is fed via a conduit 56 to the desorber 8 which likewise takes the form of a constituent of the post-combustion capture (PCC) plant 5. The heat required for the desorption in the desorber 8 is provided and supplied in the form of steam in a customary manner in a reboiler 9. In the working example, this steam is taken from the water/steam circuit 54 at a temperature of 110° C. and 200° C. as bleed steam 12 between a medium-pressure turbine 10 and a low-pressure turbine 11 of the turbogenerator 58 disposed in the water/steam circuit 54 and fed via a conduit 57 to the reboiler 9. The condensate that arises in the reboiler 9 in the reboiler heating is recycled via a conduit 13 into the preheating zone of the water/steam circuit 54. Departing from the desorber 8 are firstly the scrubbing agent which has been freed of $CO_2$ and is typically recycled in the circuit to the absorber 7, and secondly a mixture of carbon dioxide ($CO_2$) and steam. This carbon dioxide/steam mixture, after a cooling and re-scrubbing operation 14 which is disposed in the exit region of the desorber 8, is fed to a compressor stage 15. The cooling in the top region of the desorber 8 is effected with the aid of a heat exchanger 16b, and the re-scrubbing 14 is preferably effected with the aid of an acidic medium. In the compressor stage 15, the carbon dioxide/steam mixture is compressed to a pressure of above 20 bar, preferably to a pressure between 30-60 bar. The tangible heat of the carbon dioxide/steam mixture leaving the desorber 8 and the compressor stage 15 and also some of the heat of condensation of the water present therein is withdrawn or decoupled in a heat exchanger 16a which is connected downstream of the compressor stage and through which the carbon dioxide/steam mixture flows, and the dedicated heat exchanger 16b of the exit region of the desorber 8. The thermal energy withdrawn or decoupled here is fed, for example via heat exchangers 17a, 17b, 17c, 17d for the low-pressure preheater (17b) of the water/steam circuit 54, for the combustion air preheater (17a) or for reactant preheaters (17c, 17d) in the region of the reactors (27, 31) for the methanol synthesis and the distillation of a synthesis plant 60 for preparation of methanol and/or methanol conversion products. In the compressor plant which, in the working example, comprises several compressor stages 15, the heat exchanger 16a is disposed between the first and last compressor stages 15. The $CO_2$-rich gas stream 59 leaving the last compressor stage 15 is fed to a storage means 18 and thence to the synthesis plant 60 for preparation of methanol and/or methanol conversion products. Upstream of the entrance into the storage means 18, the $CO_2$-rich gas stream once again passes through a heat exchanger 19 in which this gas stream is cooled further. After leaving the storage means 18 and before entering the methanol synthesis reactor 27 of the synthesis plant 60 as well, the $CO_2$-rich gas stream flows through a further heat exchanger 20, by means of which heat is introduced into the $CO_2$-rich gas stream, in order to bring the $CO_2$-rich gas stream which enters the methanol synthesis reactor 27 as reactant to a reactor or reaction temperature in the range of 100-400° C., preferably of 150-300° C. The heat required for the purpose is fed to the heat exchanger 20 as bleed steam which is taken from the turbogenerator 58, or in the form of waste heat that arises in other processes.

In the methanol synthesis reactor, the $CO_2$ supplied in the $CO_2$-rich gas stream is reacted with hydrogen to give methanol. The hydrogen is prepared in an electrolysis plant 61 which, in the working example, is an alkaline water electrolysis. An alternative option is to employ other electrolyzer types such as polymer electrolyte membrane (PEM) electrolyzers or solid oxide electrolyzer cells (SOEC) or a chlor-alkali electrolysis.

The alkaline water electrolysis in the working example comprises an electrolysis cell 21 in which water 34 supplied is broken down electrolytically at a temperature between 50 and 100° C., preferably between 70 and 90° C., into its hydrogen and oxygen constituents. In this electrolysis, the temperature of the electrolysis cell 21 itself is controlled by means of a heat exchanger 22b and that of the water supplied by means of a heat exchanger 22a, such that the electrolysis at any time is within the optimal operating temperature range and can undergo changes in load rapidly, more particularly including those up to higher loads. The alkaline electrolysis can be operated within wide pressure ranges, especially employing pressures above 15 bar, preferably pressures in the range from 20 bar to 60 bar. Alternatively or additionally, the synthesis plant 61 is equipped with a hydrogen compressor 23 to which the hydrogen produced in the electrolysis cell 21 is fed prior to entry thereof into the methanol synthesis reactor 27. Such a hydrogen compressor 23 is appropriate especially because it has a dedicated hydrogen storage means 24 in which hydrogen produced can be stored. The intermediate storage means 24 is firstly a product storage means, since the hydrogen produced by means of the electrolysis plant 61 is stored therein. Secondly, however, it is also a reactant storage means since the hydrogen stored therein constitutes one starting material for the methanol synthesis. In order to cool the hydrogen compressed in the hydrogen compressor 23 prior to the intermediate storage thereof, a heat exchanger 25 disposed between the hydrogen compressor 23 and the intermediate storage means 24 can be used to extract or withdraw thermal energy from the hydrogen stream. In order to bring the hydrogen stream which leaves the intermediate storage means 24 at a later stage to a sufficiently high reaction temperature prior to entry thereof into the methanol synthesis reactor 27, a further heat exchanger 26 is provided, by means of which heat is introduced again into the hydrogen stream, for which purpose the heat needed may originate from the bleed steam that originates from the water/steam circuit 54 or from the waste heat from the methanol synthesis reactor 27. The rest of the waste heat that arises in the methanol synthesis can be removed via the heat exchangers or cooling units 28a, 28b, 28c which are connected downstream of the methanol synthesis reactor 27 or integrated therein. The heat exchanger 28a conducts its heat away to the preheating zone of the water/steam circuit 54, although it is also possible to conduct the heat removed away to the reboiler 9 of the post-combustion capture (PCC) plant 5 and/or to various reactant preheaters, i.e. the preheating in the power plant of the invention to give starting materials to be processed/converted. Since the conversion of the carbon dioxide ($CO_2$) and hydrogen ($H_2$) reactants supplied which is achieved in the methanol synthesis reactor 27 is not very high but is only in the range of 10%-35%, in the working example, the cooler 28a, 28b, 28c which is connected downstream and comprises the heat exchangers/cooling units is designed in such a way that a phase separation of the methanol product produced in the methanol synthesis reactor 27 is effected in a vessel 29 and the gaseous constituents removed are recycled wholly or partly via a recycle line 30 back into the methanol synthesis reactor 27. In the recycle line 30, heat is again supplied to the recycled gaseous constituents by means of the heat exchanger 17c.

The liquid phase removed in the vessel 29 is fed to a distillation or rectification reactor 31 in which water, but if desired also higher-boiling alcohols when a relatively high purity of the methanol product to be produced is desired, are separated from the liquid phase. The heat required for the distillation or rectification is appropriately provided by heat exchangers which can be supplied with lower-value bleed steam from the water/steam circuit 54 and/or from the waste heat of the reboiler 9, or else thermal energy extracted from other process steps. Departing from the distillation and/or rectification reactor 31 is a gaseous methanol ($CH_3OH$) stream 35, a particular possibility being that of extracting the heat of evaporation thereof in two subsequent cooling steps (32a, 32b) by means of heat exchangers 32a, 32b into the preheating zone of the water/steam circuit 54 and/or a reactant preheater.

The water 33 removed from the distillation and/or rectification reactor 31 can be fed to a special water processing plant and/or the feed water processing plant of the water/steam circuit 54 and then fed as reactant (water 34) to the electrolysis plant 61.

The oxygen formed in the electrolysis can be compressed, liquefied if desired, and sent to a use.

Figure 2:
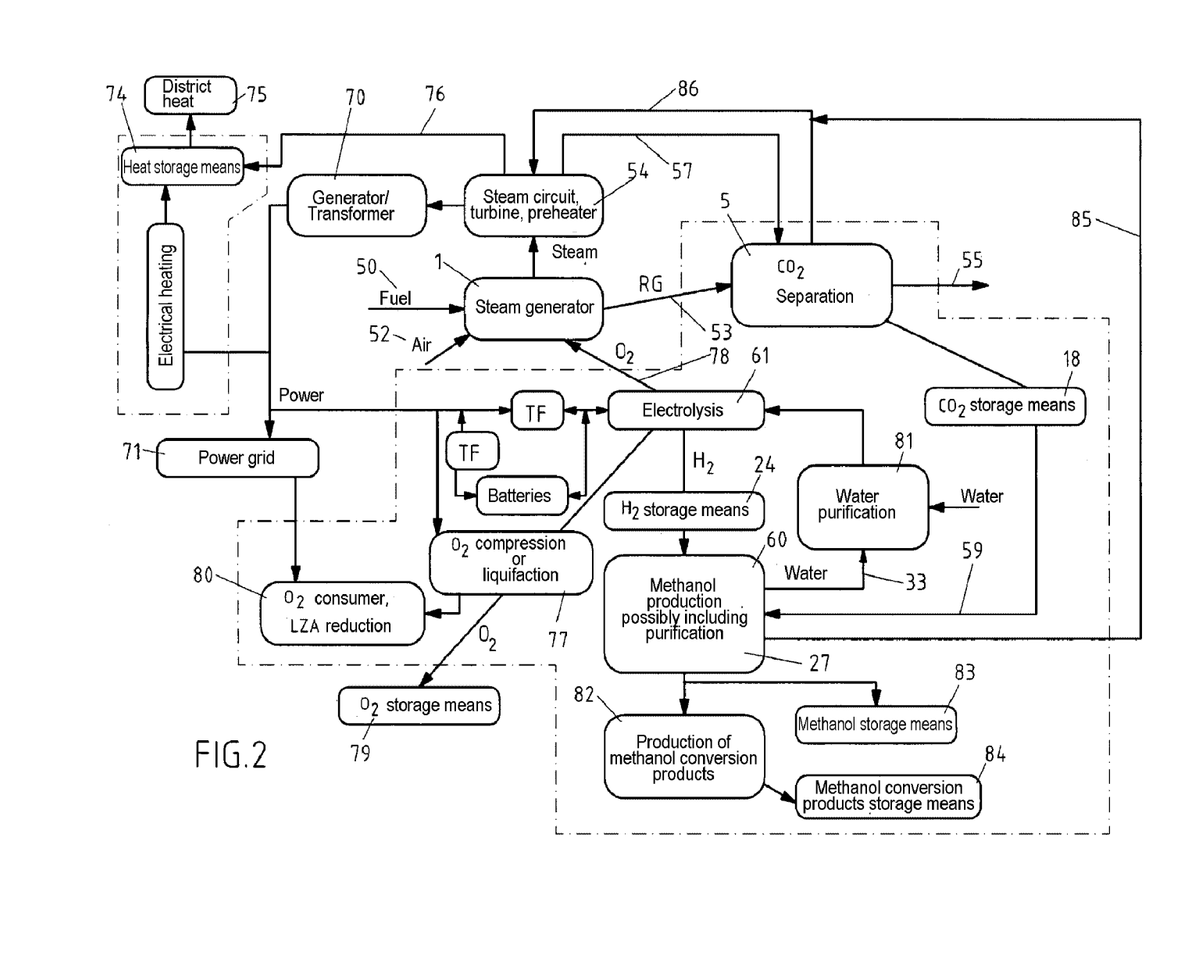

FIG. 2 shows a schematic of the assignment and interconnection of the individual units and plants of the power plant of the invention.

The power generated by means of a generator 70 with an optionally dedicated transformer in the power plant 51 can firstly be fed into the connected public power grid 71, or alternatively to the electrolysis plant 61, the electrolysis plant 61 additionally having dedicated batteries 72 and transformers 73 which enable storage and transformation of the power supplied. Alternatively, the power generated by the generator 70 can also be used to supply an electrically heated heat storage means 74 which produces district heat, for example, which can be supplied to a district heating grid 75. The heat storage means 74 can additionally be supplied with steam 76 originating from the water/steam circuit 54 or thermal energy extracted therefrom. The power generated by means of the generator 70 can alternatively be fed to an oxygen compression or liquefaction plant 77 in which oxygen 78 formed in the electrolysis 61 is processed. The compressed or liquefied oxygen can then be stored in an oxygen storage means 79 or alternatively sent to a further use 80. The oxygen 78 produced in the electrolysis plant 61 can alternatively be fed to the steam generator 1 as oxidizing agent. The individual plants or units 61, 72, 74, 77 and 80 supplied with the power generated by the generator 70 can alternatively—even though this is not shown in FIG. 2—all be supplied with power drawn from the power grid 71, especially when it provides surplus power. More particularly, the units/plants shown are interconnected to one another in such a way that the power generated by means of the generator 70 or drawn from the power grid 71 can be distributed flexibly between the individual units/plant components. The priority, however, is with the methanol production, especially with the methanol production by means of the synthesis plant 60, and so the electrolysis plant 61 is basically the plant that reacts in a flexible, timely and rapid manner to grid-side power control demands with changes in load.

The electrolysis plant 61 and the synthesis plant 60 have a dedicated water purifier 81 in which the water to be supplied to the electrolysis plant 61 and the synthesis plant 60 is purified beforehand in accordance with the desired requirements.

Both the methanol production by means of the methanol synthesis reactor 27 and the production plant for production of methanol conversion products 82 have dedicated storage means, the synthesis plant 60 having a dedicated methanol storage means 83 and the production plant 82 having a dedicated methanol conversion product storage means 84. The waste heat that arises in the methanol production in the synthesis plant 60 and that which arises in the $CO_2$ separation in the post-combustion capture plant 5 is introduced back into the water/steam circuit 54, as indicated by the arrows 85 and 86.

Overall, the power plant 51 of the invention, by virtue of the current-conducting and media-conducting connecting conduits shown in FIGS. 1 and 2, is flexibilized with regard to modes of operation that can thus be realized and production or conversion outputs that can be established or production or conversion products that can be produced. The current consumptions or current/power consumptions of the individual plant components, especially of the electrolysis plant 61, also contribute to this by enabling ways of running or modes of operation of the power plant 51 that can be adjusted to different power demands and power control demands for flexibilization. For instance, the $CO_2$ separation by means of the PCC plant 5 and/or the hydrogen production by means of the electrolysis plant can be controlled in such a way that the minimum load of the power plant 51 and the power feed-in into the power grid 71 can be reduced down to 0 $MW_{el}$. If power is then additionally drawn from the power grid 71, the grid feed-in of the power plant 51 then even becomes negative overall.

The electrolysis plant 61 can additionally be designed in such a way that the power drawn for hydrogen production is five to ten times higher than the current output of the generator 70 at each present load state of the power plant 51.

It is also possible for the $CO_2$ separation plant 5 to be designed such that up to 95% of the carbon dioxide or carbon dioxide stream produced with the flue gas 53 is separated out and, at the same time or with a time delay after intermediate storage in a $CO_2$ storage means 18, is supplied to chemical reactors, especially the methanol synthesis reactor 27 for preparation of methanol or methanol conversion products.

The storage means provided, $CO_2$ storage means 18, hydrogen storage means 24, methanol storage means 83, oxygen storage means 79 and methanol conversion product storage means 84, take the form of buffer storage means in order to be able to intermediately store the products stored therein as reactants for the downstream further processing. In this case, the hydrogen storage means 24 and/or the $CO_2$ storage means 18 and/or the oxygen storage means 79 preferably take the form of pressurized storage means and all storage means are equipped with a capacity to store the amounts of products required for the further processing, such that they can be stored for short or longer periods, but can also, if desired, be provided at short notice to the assigned production process.

In addition, the electrolysis plant 61 and/or the $CO_2$ separation plant 5 or the unit for production of a $CO_2$-rich gas stream and/or the chemical reactors, especially the methanol synthesis reactor 27, promote the flexible operation of the power plant by the provision of a rapid change in load, in such a way that the entire control capacity, especially the primary and secondary control of the power plant, is improved in relation to a power feed-in or a power consumption. The effect of the load change capacity provided by these plants, but especially the electrolysis plant 61, is that the power plant 51 can then be operated with a load change gradient of 3%/m to 10 to more than 20%/m. Of course, it is also possible to additionally provide plants in the power plant that generate renewable energy, such as photovoltaic plants or wind power plants, which then likewise provide the power generated to the overall process.

The process heat that arises or process heat required in each of the plants detailed in the individual processes can be provided by appropriate conduit interconnection of the individual plants or process components. For instance, it is possible to use process heat, especially in the range from 30 to 150° C., which is withdrawn as waste heat from the post-combustion capture plant 5 and/or as bleed steam from the water/steam circuit 54, for preheating of process streams for an electrolyzer, especially for the electrolysis plant 61, and/or for trace heating thereof and/or for preheating of reactants to be converted in the methanol synthesis reactor 27 and/or for feed water preheating in the water/steam circuit 54 and/or in the distillation and/or rectification reactor 31. It is also possible to feed waste heat which originates from the cooling of products in the reactant preheating for the electrolysis, from reactors or from the purification of products back to the overall process. It is also possible to feed the water 33 obtained in the distillation or rectification or any water obtained elsewhere in the overall process, preferably after treatment in a water purifier 81, back to the electrolysis plant 61. The oxygen formed in the electrolysis of water can be fed at least partly to an adjacent industrial operation and reduce the capacity utilization of air fractionation plants therein. Alternatively, it is possible to at least partly compress the oxygen formed in the electrolysis of water and to dispense it into pressure vessels or at least into an oxygen storage means 79 and/or liquefy it by a refrigeration process.

The dimensions of the hydrogen production and/or other plant components, especially electrical plant components, are such that it is possible to increase the electrical consumption to more than 100% of the design value, preferably to more than 120% to 200%, at least over a short period in the range of minutes, preferably up to more than 30 minutes. In addition, the dimensions of the additionally installed batteries 72 are such that it is possible to increase the electrical consumption or the electrical feed-in to more than 100% of the design value, preferably to more than 150% to 300%, at least over a short period in the range of seconds, preferably even up to more than 15 minutes.

In addition, it may be the case that an electrical water heater and/or steam generator installed in the overall process or in the power plant 51 firstly makes a contribution in relation to its power consumption to the flexibilization of the power plant, and the heat generated thereby (hot water or steam) can be fed to one or more heat storage means. More particularly, it is therefore also the case that heat storage in the form of water, steam or solids or liquids such as salts is integrated within the power plant. It is also possible for the heat generated or stored to be utilized for the drying of the fuel used, especially the brown coal envisaged in the working example, by using waste heat from the component processes or turbine bleeding (turbogenerator) for drying of brown coal or other fuels.

FIG. 1 includes the following abbreviations: GP=gas phase, FP=liquid phase, HDV=high-pressure preheater, NDV=low-pressure preheater, HD=high-pressure turbine, MD=medium-pressure turbine and ND=low-pressure turbine.

Finally, it may also be the case that some of the reaction products produced, especially with the synthesis plant 60, i.e. methanol or a methanol conversion product, are stored at the power plant site and supplied at least temporarily as starter fuel and/or as support fuel and/or as main fuel to the burners of the steam generator 1 and combusted therein.

A $CO_2$-rich gas stream in the context of this application is understood to mean one having a proportion of at least 12, especially at least 30, percent by weight or percent by volume of $CO_2$.

In summary, it can be stated that the invention proceeds from the consideration that, in the case of power plants that would otherwise have to be run down, the increase in the internal demand for energy by means of the $CO_2$ separation 5 (especially demand for steam for the heating of the reboiler 9) and by means of a methanol preparation by a synthesis plant 60 (demand for power for the electrolysis) can increase the exploitation of the existing power plant capacities by making it possible to operate the power plant with a higher load even in periods of weak demand than would be necessary for pure power generation. The ultimate outcome is that the power plant can then be operated with a higher number of full-load hours, since it is not just designed for power production but also for methanol production or the production of methanol conversion products. In addition, the invention is based on the consideration that the higher speed of change in the load of the electrolysis plant 61 compared to the possible speed of change in the load of the power plant can be utilized in order to offer a much quicker control service to the connected public power grid. In the event of power control or a power control demand from the power grid side, the electrolysis plant 61 can be run up or run down relatively quickly and at short notice, such that the steam generator or the power plant overall is given more time to undertake a change in load, or there is even avoidance of any need for a change in load of the actual power plant component, i.e. an adjustment of the output of the steam generator 1. Finally, the invention proceeds from the consideration that it is possible with the invention to avoid the need to shut down the power plant entirely in times of weak demand. It can still be designed such that the electrolysis plant 61 and the methanol production 60 draw or consume sufficient power at minimum load of the power plant and no power release to the grid becomes necessary.

Marginal cases for the inventive design of a power plant are firstly brown coal power plants which currently (still) generate electrical power very inexpensively. Such a power plant can still be run at 100% load (full load) with the invention, even when the power grid does not consume the electrical power generated in the form of power. The unconsumed power can be utilized in the electrolysis plant 61 for production of hydrogen. The other marginal case is that of hard coal power plants which nowadays have to be run with a minimum load since they would otherwise take too long to restart, or which have to keep a specific generator output available for control purposes. In the case of hard coal power plants equipped in accordance with the invention, the minimum load can now be (over-)absorbed and the power generated can be utilized for the hydrogen production in the electrolysis plant 61 without any need to remove the power plant from the grid, such that the high-inertia rotating mass thereof (especially that of the generator) is still available to the grid for control support.

In this respect, flexibilization of the mode of operation of a power plant is enabled, since the actual power plant 51 can still gradually change its load, but the load utilized by the electrolysis plant 61 and the synthesis plant 60 is available for control.

Overall, the aforementioned control options can improve the economic viability of a power plant (more full-load hours, constantly available grid services, additional "fuel" product (methanol and methanol conversion products)).

It is advantageous in the case of the present invention that there is no need for prior gasification of products for preparation of methanol or methanol conversion products; instead, the combustion of carbonaceous fuel in the steam generator 1 of a/the power plant 51 is utilized. The invention features low capital costs in the retrofitting of existing power plants, an increase in the economic viability of existing plants in the case of retrofitting and high operational safety and reliability of the methanol synthesis which uses $CO_2$ formed in the combustion in the steam generator 1 and $H_2$ produced by electrolysis. Even in the case of new constructions, the inventive solution constitutes an improvement in flexibility, plant exploitation time and economic viability.

In the power plant shown in schematic form in FIG. 1, for example, in the operation of a 670 MWel power plant at 30% load, 45 kg/s of fuel (calorific value 10.5 MJ/kg) are required, 190 Mel of power are generated, 15% of the $CO_2$ present in the flue gas is separated out and 1.1 kg/s of hydrogen are produced electrolytically. From the latter are produced about 6 kg/s of methanol, which corresponds to a carbon conversion efficiency of the fuel to the methanol product of about 27% and an efficiency of more than 60% (power to calorific value of the methanol).

If these product volumes were produced in each of 90% of the annual operating hours of such a power plant, assuming fuel costs of 10 €/t and sales of 400 €/t of methanol, it would be possible to achieve a turnover of million Euros. In addition, the power plant may generate additional sales through higher power production, and primary/secondary control for virtually the whole year. Finally, sales are also possible through demand-side management by means of the electrolysis plant 61. More particularly, the electrolysis plant 61 itself can at any time run loads between 0 and up to more than 200 MW, in some cases up to 400 MW (overloads only briefly), much more quickly than the power plant, and so it is possible to provide additional grid services.

It is apparent from this that the inventive flexibilization of the power plant 51 has a positive influence on the operation of the power plant 51 both in technical and economic terms.

The invention claimed is:

1. A power plant which has a large-scale steam generator which is equipped with carbon-fired burners and/or a gas turbine and has a connected water/steam circuit comprising at least one steam-charged turbogenerator comprising at least one connected generator, wherein a $CO_2$-containing offgas stream is produced in the large-scale steam generator equipped with the carbon-fired burners, and which comprises at least one unit for production of a $CO_2$-rich gas stream, and which is connected by its power-generating component comprising the at least one generator to a public power grid which provides control power, wherein the release of electrical power by the power-generating component of the power plant to the power grid is subject to power control on the power grid side, wherein the power plant comprises at least one electrolysis plant for preparation of hydrogen ($H_2$) and at least one synthesis plant for preparation of methanol and/or methanol conversion products from at least $CO_2$ components of the $CO_2$-rich gas stream and the hydrogen produced in the electrolysis plant, and wherein the at least one unit for production of a $CO_2$-rich gas stream and the at least one electrolysis plant for preparation of hydrogen ($H_2$) and the at least one synthesis plant for preparation of methanol and/or methanol conversion products from at least CO$_2$ components of the CO$_2$-rich gas stream and the hydrogen produced in the electrolysis plant are connected and interconnected physically and electrically to one another in terms of conduction via current-conducting and via media-conducting lines to form a group in such a way that the power generated on the power plant side in the course of operation of the power plant is utilizable wholly or partly, as required, for operation of one, more than one or all of this group of units and plants comprising the at least one unit for production of a CO$_2$-rich gas stream, the at least one electrolysis plant for preparation of hydrogen (H$_2$) and the at least one synthesis plant for preparation of methanol and/or methanol conversion products.

2. The power plant as claimed in claim 1, wherein the at least one electrolysis plant for preparation of hydrogen (H$_2$) or a plurality of electrolysis plants for preparation of hydrogen (H$_2$) is/are designed and set up on the power plant side in terms of their current/power consumption capacity and their hydrogen production capacity so as to be controllable in such a way that the current/power consumption and hydrogen production thereof can be run up or down within 5 minutes, in response to a grid-side power control demand on the power plant.

3. The power plant as claimed in claim 1, wherein the at least one unit for production of a CO$_2$-rich gas stream or a plurality of units for production of a CO$_2$-rich gas stream and/or the at least one synthesis plant for preparation of methanol and/or methanol conversion products from at least portions of the CO$_2$-rich gas stream or a plurality of synthesis plants for preparation of methanol and/or methanol conversion products from at least portions of the CO$_2$-rich gas stream is/are designed and set up on the power plant side in terms of their current/power consumption capacity and their production or conversion capacity so as to be controllable in such a way that their respective current/power consumption and production or conversion output can be run up or down within 5 minutes, in response to a grid-side power control demand on the power plant.

4. The power plant as claimed in claim 1 wherein the at least one electrolysis plant for preparation of hydrogen (H$_2$) or the plurality of electrolysis plants for preparation of hydrogen (H$_2$) and the at least one unit for production of a CO$_2$-rich gas stream or the plurality of units for production of a CO$_2$-rich gas stream and the at least one synthesis plant for preparation of methanol and/or methanol conversion products from at least portions of the CO$_2$-rich gas stream or the plurality of synthesis plants for preparation of methanol and/or methanol conversion products from at least portions of the CO$_2$-rich gas stream are designed and connected to one another for control purposes on the power plant side in terms of their respective current/power consumption capacity and their respective production or conversion output in such a way that they can be run up or down in response to a grid-side power control demand on the power plant in the integrated system, each in terms of their respective current/power consumption and production or conversion output, within 5 minutes, that the power plant, in the case of a grid-side power control demand, can be adjusted to the altered power demand in terms of output by way of a change in load with a load change gradient in the range of 3%/min-30%/min.

5. The power plant as claimed in claim 1 wherein the at least one electrolysis plant for preparation of hydrogen (H$_2$) or the plurality of electrolysis plants for preparation of hydrogen (H$_2$) and the at least one unit for production of a CO$_2$-rich gas stream or the plurality of units for production of a CO$_2$-rich gas stream and the at least one synthesis plant for preparation of methanol and/or methanol conversion products from at least portions of the CO$_2$-rich gas stream or the plurality of synthesis plants for preparation of methanol and/or methanol conversion products from at least portions of the CO$_2$-rich gas stream is/are designed in terms of their respective current/power consumption and/or their respective production or conversion output in such a way that it/they can be subjected, in response to a grid-side power control demand on the power plant, for short periods within a period of up to 30 minutes, to a current/power consumption of 100%-300% of the standard design or standard operating value for the particular plant or unit.

6. The power plant as claimed in claim 1 wherein the at least one electrolysis plant for preparation of hydrogen (H$_2$) or the plurality of electrolysis plants for preparation of hydrogen (H$_2$) and the at least one unit for production of a CO$_2$-rich gas stream or the plurality of units for production of a CO$_2$-rich gas stream and the at least one synthesis plant for preparation of methanol and/or methanol conversion products from at least portions of the CO$_2$-rich gas stream or the plurality of synthesis plants for preparation of methanol and/or methanol conversion products from at least portions of the CO$_2$-rich gas stream are configured to be able to be actuated and controlled individually in terms of their respective current/power consumption and their respective production or conversion output.

7. The power plant as claimed in claim 1 wherein the at least one synthesis plant for preparation of methanol and/or methanol conversion products or the plurality of synthesis plants for preparation of methanol and/or methanol conversion products is/are designed overall in terms of capacity such that it/they can be used to convert 10%-50% by weight of the CO$_2$ which forms at full load of the power plant and is present in the CO$_2$-containing offgas stream to methanol and/or a methanol conversion product.

8. The power plant as claimed in claim 1 wherein the at least one synthesis plant for preparation of methanol and/or methanol conversion products or the plurality of synthesis plants for preparation of methanol and/or methanol conversion products is/are designed overall with regard to their current/power consumption capacity and the production or conversion output possible in each case, in terms of capacity, such that not more than the total amount of electrical power that can be generated by the power plant at full load and/or maximum power thereof can be utilized for the preparation of methanol and/or methanol conversion products.

9. The power plant as claimed in claim 1 wherein the at least one unit for production of a CO$_2$-rich gas stream or the plurality of units for production of a CO$_2$-rich gas stream comprise(s) or consist(s) of at least one CO$_2$ separation plant, and/or one or more burner(s) or burner device(s), operated by the oxyfuel process, of the large-scale steam generator having a dedicated CO$_2$ separation plant.

10. The power plant as claimed in claim 1 wherein the at least one electrolysis plant for preparation of hydrogen (H$_2$) or the plurality of electrolysis plants for preparation of hydrogen (H$_2$) and the at least one unit for production of a CO$_2$-rich gas stream or the plurality of units for production of a CO$_2$-rich gas stream and the at least one synthesis plant for preparation of methanol and/or methanol conversion products from at least portions of the CO$_2$-rich gas stream or the plurality of synthesis plants for preparation of methanol and/or methanol conversion products from at least portions of the CO$_2$-rich gas stream are designed with regard to their current/power consumption and production or conversion output overall in such a way that, in the course of operation thereof, the power plant can be operated in operation with its minimum load necessary for the purposes of the plant without feeding power into the power grid.

11. The power plant as claimed in claim 1 wherein the power plant takes the form of a power sink for the connected public power grid, in which case the at least one electrolysis plant for preparation of hydrogen ($H_2$) or the plurality of electrolysis plants for preparation of hydrogen ($H_2$) and the at least one unit for production of a $CO_2$-rich gas stream or the plurality of units for production of a $CO_2$-rich gas stream and the at least one synthesis plant for preparation of methanol and/or methanol conversion products from at least portions of the $CO_2$-rich gas stream or the plurality of synthesis plants for preparation of methanol and/or methanol conversion products from at least portions of the $CO_2$-rich gas stream are designed in terms of their current/power consumption and production or conversion output overall and are connected to the power grid in such a way that they can be operated with the surplus power drawn from the power grid.

12. The power plant as claimed in claim 1 wherein the at least one electrolysis plant for preparation of hydrogen ($H_2$) or the plurality of electrolysis plants for preparation of hydrogen ($H_2$) and the at least one unit for production of a $CO_2$-rich gas stream or the plurality of units for production of a $CO_2$-rich gas stream and the at least one synthesis plant for preparation of methanol and/or methanol conversion products from at least portions of the $CO_2$-rich gas stream or the plurality of synthesis plants for preparation of methanol and/or methanol conversion products from at least portions of the $CO_2$-rich gas stream are connected physically and electrically to the public power grid as a load that can be switched off.

13. The power plant as claimed in claim 1 wherein the at least one electrolysis plant for preparation of hydrogen ($H_2$) or the plurality of electrolysis plants for preparation of hydrogen ($H_2$) and the at least one unit for production of a $CO_2$-rich gas stream or the plurality of units for production of a $CO_2$-rich gas stream and the at least one synthesis plant for preparation of methanol and/or methanol conversion products from at least portions of the $CO_2$-rich gas stream or the plurality of synthesis plants for preparation of methanol and/or methanol conversion products are conductively connected in terms of waste heat that arises in the operation of these plant(s) and/or unit(s) in the range of 30-400° C. via at least one waste heat-conducting conduit to a preheater of the feed water of the water/steam circuit and/or a preheater of a $CO_2$ separation plant, and/or a preheater of at least one of the in reactants used and/or products generated in the power plant.

14. The power plant as claimed in claim 1 wherein the at least one electrolysis plant for preparation of hydrogen ($H_2$) or the plurality of electrolysis plants for preparation of hydrogen ($H_2$) is/are designed in terms of their production and/or conversion capacity in such a way that the amount of hydrogen that can be produced can be used to convert the entire $CO_2$ content of the offgas stream that forms in the burners of the large-scale steam generator in the course of combustion of carbonaceous fuel and/or the total amount of $CO_2$ separated out in the at least one $CO_2$ separation plant to methanol or a methanol conversion product in the synthesis plant(s) for preparation of methanol and/or methanol conversion products.

15. The power plant as claimed in claim 1 wherein each of the units or plants from the group of the at least one unit for production of a $CO_2$-rich gas stream, the at least one electrolysis plant for preparation of hydrogen ($H_2$) and the at least one synthesis plant for preparation of methanol and/or methanol conversion products has at least one dedicated reactant and/or product storage component, and the electrolysis plant has a dedicated hydrogen storage component and/or an oxygen storage component and the unit for production of a $CO_2$-rich gas stream has a dedicated $CO_2$ storage component.

16. A method of flexibly operating a power plant as claimed in claim 1 wherein the at least one unit for production of a $CO_2$-rich gas stream and the at least one electrolysis plant for preparation of hydrogen ($H_2$) and the at least one synthesis plant for preparation of methanol and/or methanol conversion products from at least $CO_2$ components of the $CO_2$-rich gas stream and the hydrogen produced in the electrolysis plant have been and are connected and interconnected physically and electrically to one another in terms of conduction by current-conducting and media-conducting lines to form a group such that the power generated on the power plant side in the course of operation of the power plant is utilized wholly or partly, as required, for operation of one, more than one or all of this group of units and plants comprising the unit for production of a $CO_2$-rich gas stream, the electrolysis plant for preparation of hydrogen ($H_2$) and the synthesis plant for preparation of methanol and/or methanol conversion products.

17. The method as claimed in claim 16, wherein the current/power consumption and the hydrogen production in the at least one electrolysis plant for preparation of hydrogen ($H_2$) or the plurality of electrolysis plants for preparation of hydrogen ($H_2$) is run up or down within 5 minutes, on the power plant side in response to a grid-side power control demand on the power plant.

18. The method as claimed in claim 16 wherein the respective current/power consumption and production or conversion output of the at least one unit for production of a $CO_2$-rich gas stream or a plurality of units for production of a $CO_2$-rich gas stream and/or the at least one synthesis plant for preparation of methanol and/or methanol conversion products from at least portions of the $CO_2$-rich gas stream or a plurality of synthesis plants for preparation of methanol and/or methanol conversion products from at least portions of the $CO_2$-rich gas stream is run up or down within 5 minutes, on the power plant side in response to a grid-side power control demand on the power plant.

19. The method as claimed in claim 16 wherein the at least one electrolysis plant for preparation of hydrogen ($H_2$) or the plurality of electrolysis plants for preparation of hydrogen ($H_2$) and the at least one unit for production of a $CO_2$-rich gas stream or the plurality of units for production of a $CO_2$-rich gas stream and the at least one synthesis plant for preparation of methanol and/or methanol conversion products from at least portions of the $CO_2$-rich gas stream or the plurality of synthesis plants for preparation of methanol and/or methanol conversion products from at least portions of the $CO_2$-rich gas stream are actuated and controlled individually in terms of their respective current/power consumption and their respective production or conversion output.

20. The method as claimed in claim 16 wherein the at least one electrolysis plant for preparation of hydrogen ($H_2$) or the plurality of electrolysis plants for preparation of hydrogen ($H_2$) and the at least one unit for production of a $CO_2$-rich gas stream or the plurality of units for production of a $CO_2$-rich gas stream and the at least one synthesis plant for preparation of methanol and/or methanol conversion products from at least portions of the $CO_2$-rich gas stream or the plurality of synthesis plants for preparation of methanol and/or methanol conversion products from at least portions of the $CO_2$-rich gas stream are operated as a load connected physically and electrically to the public power grid that can be switched off.

21. A power plant comprising:
   a steam generator configured to produce electricity and a $CO_2$-containing offgas stream;
   a first current-conducting line configured to conduct the electricity produced by the steam generator to a power grid, the conduction of electricity to the power grid subject to control from the power grid;
   a $CO_2$ separation unit configured to process the $CO_2$-containing offgas stream to produce a $CO_2$-rich gas stream;
   a first media-conducting line conducting the $CO_2$-containing offgas stream from the steam generator to the $CO_2$ separation unit;
   a second current-conducting line configured to conduct electricity produced by the steam generator to the $CO_2$ separation unit;
   a synthesis plant for production of at least one of methanol and methanol conversion products from hydrogen ($H_2$) and the $CO_2$-rich gas stream, the synthesis plant also producing water;
   a second media-conducting line conducting the $CO_2$-rich gas stream from the $CO_2$ separation unit to the synthesis plant;
   a third current-conducting line configured to conduct electricity produced by the steam generator to the synthesis plant;
   an electrolysis plant configured to produce hydrogen ($H_2$) from water;
   a third media-conducting line conducting water from the synthesis plant to the electrolysis plant;
   a fourth media-conducting line conducting hydrogen ($H_2$) from the electrolysis plant to the synthesis plant; and
   a fourth current-conducting line configured to conduct electricity produced by the steam generator to the electrolysis plant, wherein the electricity generated by the steam generator is conducted to one or more of the electrolysis unit, the synthesis unit, and the $CO_2$ separation unit, based on the control from the power grid, for operation of one or more of the electrolysis unit, the synthesis unit, and the $CO_2$ separation unit.

22. The power plant of claim 21, wherein the power plant is configured to adjust the power consumption of the electrolysis plant, in response to control from the power grid, to increase or decrease the power provided to the power grid by the power plant.

23. The power plant of claim 1, wherein the power plant is configured to adjust the power consumption of the at least one electrolysis plant in response to a grid-side power control demand on the power plant from the power grid.

* * * * *

UNITED STATES PATENT AND TRADEMARK OFFICE
CERTIFICATE OF CORRECTION

PATENT NO. : 9,885,257 B2
APPLICATION NO. : 14/904057
DATED : February 6, 2018
INVENTOR(S) : Christian Bergins et al.

It is certified that error appears in the above-identified patent and that said Letters Patent is hereby corrected as shown below:

On the Title Page

In Column 2 (item (56)) at Line 12, Under Other Publications, change "20148004978.4." to --201480049578.4.--.

Item (57), (Abstract) at Line 7, Change "part," to --part--.

Item (57), (Abstract) at Line 9, Change "controlled," to --controlled--.

In the Specification

In Column 17 at Line 25, After "plant" insert --61--.

In Column 20 at Line 29, After "of" insert --60--.

In the Claims

In Column 23 at Line 54, In Claim 14, change "($H_z$)" to --($H_2$)--.

Signed and Sealed this
Fifteenth Day of May, 2018

Andrei Iancu
*Director of the United States Patent and Trademark Office*